United States Patent
Subramaniam

(10) Patent No.: US 9,149,187 B2
(45) Date of Patent: Oct. 6, 2015

(54) ONLINE MONITORING OF PATIENT FOR ROUTINE CHECKUPS

(75) Inventor: Rajendran Subramaniam, Tucson, AZ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1723 days.

(21) Appl. No.: 12/354,974

(22) Filed: Jan. 16, 2009

(65) Prior Publication Data
US 2010/0185711 A1 Jul. 22, 2010

(51) Int. Cl.
G06F 7/00 (2006.01)
G06F 17/30 (2006.01)
A61B 5/00 (2006.01)
G06F 19/00 (2011.01)
A61B 5/021 (2006.01)
A61B 5/145 (2006.01)

(52) U.S. Cl.
CPC .......... *A61B 5/0002* (2013.01); *G06F 19/3418* (2013.01); *A61B 5/021* (2013.01); *A61B 5/14532* (2013.01); *G06F 17/30569* (2013.01); *G06F 19/345* (2013.01)

(58) Field of Classification Search
CPC ................ G06F 17/30569; G06F 17/30575; G06F 15/16; G06F 19/322; G06F 19/3418; G06F 19/345; G06F 19/3412
See application file for complete search history.

(56) References Cited

U.S. PATENT DOCUMENTS

| 5,331,550 | A | * | 7/1994 | Stafford et al. | 382/128 |
| 5,953,708 | A | * | 9/1999 | Midorikawa et al. | 705/35 |
| 5,997,478 | A | * | 12/1999 | Jackson et al. | 600/437 |
| 6,287,765 | B1 | * | 9/2001 | Cubicciotti | 435/6.11 |
| 6,804,656 | B1 | * | 10/2004 | Rosenfeld et al. | 705/3 |
| 7,154,398 | B2 | * | 12/2006 | Chen et al. | 340/573.1 |
| 2003/0127037 | A1 | * | 7/2003 | Himmel | 114/361 |
| 2006/0271409 | A1 | | 11/2006 | Rosenfeld et al. | |
| 2006/0293571 | A1 | * | 12/2006 | Bao et al. | 600/300 |
| 2007/0049806 | A1 | * | 3/2007 | Adams et al. | 600/309 |
| 2007/0299316 | A1 | * | 12/2007 | Haslehurst et al. | 600/300 |
| 2008/0033303 | A1 | | 2/2008 | Wariar et al. | |
| 2008/0059239 | A1 | * | 3/2008 | Gerst et al. | 705/3 |
| 2008/0076971 | A1 | * | 3/2008 | Clapp | 600/300 |
| 2009/0114427 | A1 | * | 5/2009 | Feider et al. | 174/254 |

* cited by examiner

*Primary Examiner* — Daniel Kuddus
(74) *Attorney, Agent, or Firm* — Griffiths & Seaton PLLC

(57) ABSTRACT

A method, system, and computer program product for performing remote monitoring of a patient during a routine checkup is provided. A local server is adapted for receiving instructions from a medical professional and processing the instructions into commands for remote broadcast. A network device is in remote communication with the local server. At least one modular diagnostic tool is communicable with the network device over a standardized communications link. The at least one modular diagnostic tool is operable by the medical professional based on a second portion of the commands for remote broadcast to obtain the diagnostic information. Upon a communications connection between the modular diagnostic tool and the network device, an automated process is executed to upload the diagnostic information from the modular diagnostic tool to the local server for collection and analysis.

20 Claims, 6 Drawing Sheets

ONLINE MONITORING OF PATIENT FOR ROUTINE CHECKUPS

BACKGROUND OF THE INVENTION

1. Field of the Invention

The present invention relates in general to computers, and more particularly to apparatus, method and computer program product embodiments for online monitoring of remote medical patients by a medical professional using a data processing system.

2. Description of the Related Art

Computers and computer systems are found in a variety of settings in today's society. Computing environments and networks may be found at home, at work, at school, in government, and in other settings. Computers and computer systems, including associated data storage, are increasingly being utilized to lower costs, increase productivity, provide security, and a host of other functions.

In the medical industry, the resources of medical professionals are increasingly spread in a variety of areas. In addition, demand for care has increased, while the supply, particularly of primary care physicians, has not. As a result, an alternative mechanism to meet medical need, such as providing contact with medical professionals for regular checkups, is needed. This alternative mechanism would help the medical professional better manage the increasing demand on their available resources, principally time, and allow for greater access to care for more patients. Currently, an effort is underway to facilitate medical consultations using computers and computing systems. This current effort, as of yet, has not fully addressed the need.

SUMMARY OF THE INVENTION

In light of the foregoing, a need exists for a computer-facilitated mechanism linking a local physician interface to a remote patient interface, as well as a tool connectable to the patient interface that can read the patient's physical condition, to provide diagnostic information to the physician as well as treatment information to the patient in lieu of a face-to-face routine checkup.

Accordingly, in one embodiment, by way of example only, a system for performing remote monitoring of a patient during a routine checkup is provided. A local server is adapted for receiving instructions from a medical professional and processing the instructions into commands for remote broadcast. A network device is in remote communication with the local server. The network device is adapted for processing the commands for remote broadcast received from the local server. At least one modular diagnostic tool is communicable with the network device over a standardized communications link. The at least one modular diagnostic tool is adapted for obtaining diagnostic information from the patient. A first portion of the commands for remote broadcast includes directions to the patient for installation of the at least one modular diagnostic tool in the network device. The at least one modular diagnostic tool is initialized for operation by the network device. The at least one modular diagnostic tool is operable by the medical professional based on a second portion of the commands for remote broadcast to obtain the diagnostic information. The network device, when connected with the at least one modular diagnostic tool over the standardized communications link, executes an automated process to upload the diagnostic information to the local server for collection and analysis by the medical professional.

In an additional embodiment, again by way of example only, a method for performing remote monitoring of a patient during a routine checkup by at least one processor device in communication with a memory device is provided. Instructions from a medical professional are received on a local server. The instructions are processed into commands for remote broadcast. The commands are forwarded for remote broadcast to a network device over a network path. The commands for remote broadcast received from the local server are processed on the network device. The patient is directed to install a modular diagnostic tool in the network device using a first portion of the commands for remote broadcast. The modular diagnostic tool is initialized for operation and communication with the network device over a standardized communications link. The medical professional operates the modular diagnostic tool over the network path using a second portion of the commands for remote broadcast to obtain diagnostic information. Upon a communications connection between the modular diagnostic tool and the network device, an automated process is executed to upload the diagnostic information from the modular diagnostic tool to the local server for collection and analysis by the medical professional.

In still another embodiment, again by way of example only, a computer program product for performing remote monitoring of a patient during a routine checkup by at least one processor device in communication with a memory device is provided. The computer program product comprises a computer-readable storage medium having computer-readable program code portions stored therein. The computer-readable program code portions comprise a first executable portion for receiving instructions from a medical professional on a local server, a second executable portion for processing the instructions into commands for remote broadcast, a third executable portion for forwarding the commands for remote broadcast to a network device over a network path, a fourth executable portion for processing the commands for remote broadcast received from the local server on the network device, a fifth executable portion for directing the patient to install a modular diagnostic tool in the network device using a first portion of the commands for remote broadcast, a sixth executable portion for initializing the modular diagnostic tool for operation and communication with the network device over a standardized communications link, a seventh executable portion for operating the modular diagnostic tool by the medical professional over the network path using a second portion of the commands for remote broadcast to obtain diagnostic information, and an eighth executable portion for, upon a communications connection between the modular diagnostic tool and the network device, performing an automated process on the network device to upload the diagnostic information from the modular diagnostic the local server for collection and analysis by the medical professional.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
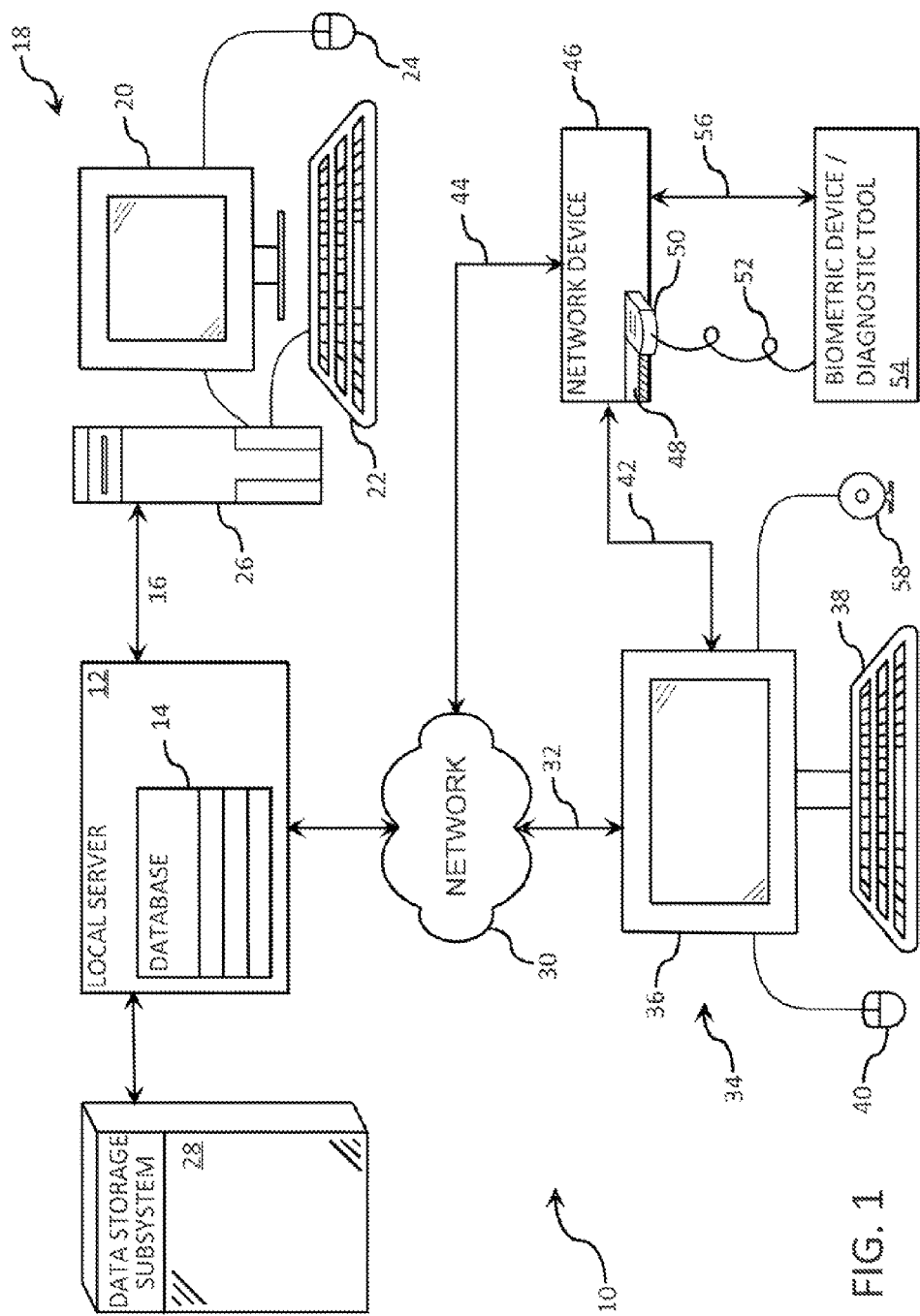
FIG. 1 illustrates an system for performing remote monitoring of a patient (such as during a routine checkup) in which aspects of the present invention may be implemented.

The illustrated embodiments below provide mechanisms for communication between a remote patient and a local medical professional over one or more communications links, whereby the medical professional is capable of providing online instruction and related assistance to the patient, while obtaining biometric information (herein also referred to as diagnostic information) from the patient using a modular diagnostic tool.

In addition, the illustrated embodiments provide, through the use of the diagnostic tool, mechanisms whereby the patient may continue to obtain information on an offline basis (either himself or by operation of other medical personnel such as a lab technician). When a connection is again made with the local medical professional, an automated process may be executed to upload the supplemental information from the diagnostic tool to the local medical professional. As will be further described, additional benefits, features, and improvements to current systems and techniques are discussed.

Embodiments of the invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, that may carry out a variety of functions under the control of one or more microprocessors or other control devices. In addition, those skilled in the art will appreciate that embodiments of the present invention may be practiced in conjunction with any number of data transmission and data formatting protocols and that the system described herein is one example embodiment of the invention.

For the sake of brevity, conventional techniques related to signal processing, data transmission, signaling, network control, the 802.11 family of specifications, wireless networks, additional communications systems and specifications, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the invention.

The following description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. The term "exemplary" is used in the sense of "example," rather than "model." Although the figures may depict example arrangements of elements, additional intervening elements, devices, features, or components may be present in an embodiment of the invention.

Referring now to FIG. 1, an exemplary system 10 for providing remote monitoring of a patient by a medical professional is depicted. System 10 includes a local server 12. An exemplary local server 12 will be described in FIG. 2, following. Local server 12, as the skilled artisan will appreciate, may include a variety of computing environments and platforms. In most cases, local server 12 includes one or more processing devices in communication with one or more memory devices. In some cases, a database 12 is operational on, or in conjunction with, the local server 12. Database 12 may store patient information, such as a history of blood glucose test results. In addition, database 12 may store drug information, such as a patient's prescription drug history as prescribed by the medical professional.

The medical professional, such as a physician or physician assistant, communicates with the local server 12 via a connected communications channel 16. As the skilled artisan will appreciate, communications channel 16 may comprise a host of available communications schemes, such as an intranet, an extranet, a wide area network (WAN), a local area network (LAN), Ethernet, wireless, and the like. Channel 16 is connected to a local interface 18. Local interface 18 includes a workstation 26 (local client) of the local server 12. Workstation 26 may also include a number of computing components, and be connected with a number of peripheral components, such as the depicted graphical user interface (GUI) 20, the keyboard 22, and mouse 24 input devices. In one embodiment, for example, the database 14 operational on local server 12 is accessed by a physician through the workstation 26 and viewed on GUI 20.

The medical professional may use the workstation 26, in combination with local server 12, to access additional patient information stored on an interconnected data storage subsystem 28. For example, the data storage subsystem 28 may store a library of drug information, such as drug interaction data, that may be accessed when the medical professional is prescribing a drug to a particular patient to obtain potential adverse drug interaction information that may be provided to the medical professional via workstation 26.

To communicate with a remote patient, local server 12 is coupled to network 30, which again, may include a host of network paths. For example, at least a portion of network 30 may include the world-wide-web (WWW). To facilitate such communication, local server 12, as well as workstation 26 and data storage subsystem 28 may be compliant with a number of communications protocols, such as transport control protocol (TCP)/internet protocol (IP).

A patient interface 34 is connected through an additional communications channel 32 to the network 30. Patient interface 34 may again include a number of computing components. In one example, the interface 34 may also include a personal computer with an integrated GUI 36, attached keyboard 38, and mouse 40. Patient interface 34 may also include additional input devices such as a webcam/microphone 58 for facilitating voice/visual input from the patient.

The medical professional supplies a network device 46 to the patient. Medical device 46 is adapted to establish communications links with the patient interface 34 and/or network 30 via communications channels 42 and 44, respectively. In this regard, network device 46 may use an existing communications channel (such as a universal serial bus, or USB) to establish a communications link between the network device 46 and the patient interface 34. Alternatively, network device 46 may include a communications adapter (as will be further described) enabling the network device 46 to establish connectivity directly to network 30 (such as by scanning available wireless networks).

Network device 46 will be further described in detail, following. As an overview of the provided functionality, network device 46 acts as an interface device for a modular diagnostic tool/biometric device 54, connecting the device 54 through the network 30 to the local server 12 to the interface 26. As with network device 46, the functionality of diagnostic tool 54 will be further explained. It should be noted that a variety of mechanisms may be implemented to connect the diagnostic tool 54 with the network device 46. One such mechanism uses wired communication 52 over a standardized communications link (in this case, a USB connection). As such, network device 46 incorporates two USB ports 48, into one of which a USB connector 50 is shown inserted. Alternatively, tool 54 may use an additional communications channel 56 (e.g., 802.xx compliant).

As will be further described, the diagnostic tool 54 is one of a variety of similar tools 54 that are may be specialized for performing specific medical functionality. For example, one diagnostic tool 54 may perform blood glucose monitoring functionality, while another diagnostic tool 54 may monitor blood pressure. Each of the tools 54, however, is modular in that they share one or more communications schemes to connect with the network device 46 using a standardized communications link. For example, each of the tools 54 may be connectable to the network device 46 using a USB communications link.

The diagnostic tool 54 may perform a wide variety of medical functionality to obtain biometric and other diagnostic information. For example, the diagnostic tool may include a blood pressure monitor, pulse oximeter, blood glucose meter, scale, thermometer, otoscope, ophthalmoscope, body fat monitor, heart rate monitor, stethoscope, alcohol screening device, fingerprint scanner, retinal scanner, and pH meter.

The use of a variety of available diagnostic tools 54 compatible with a single network device 46 allows for flexibility in providing medical services to a particular patient over system 10. For example, a particular patient with diabetes may be provided a blood glucose monitor tool 54 to routinely provide blood glucose information through system 10 to a monitoring physician. As will be seen, the blood glucose information may be stored locally on the tool 54, and/or uploaded through network device 46 to the local server 12 where it is stored on the database 14 and accessible (along with previous test information) to a monitoring physician. In addition, the tool 54 may be operable by the physician to perform specific functionality, or the tool may be disconnected from the network device and used to gather information on an offline basis that is later automatically uploaded over the network 30 to the medical professional when the tool 54 is subsequently reconnected with the network device 46.

The flexibility provided by system 10 allows the medical professional to provide medical services to a larger patient base without compromising quality of service. In addition, the medical professional may use the various components of system 12 to perform such functionality as remote diagnosis of medical conditions, and virtual communication over the network 30 with the patient to suggest follow up action items, such as an instruction to visit a laboratory for further testing or instruction in regards to a prescribed medication. This flexibility alleviates the patient from having to travel, in some cases, great distances to the offices of the medical professional for routine services and checkups.

Figure 2:
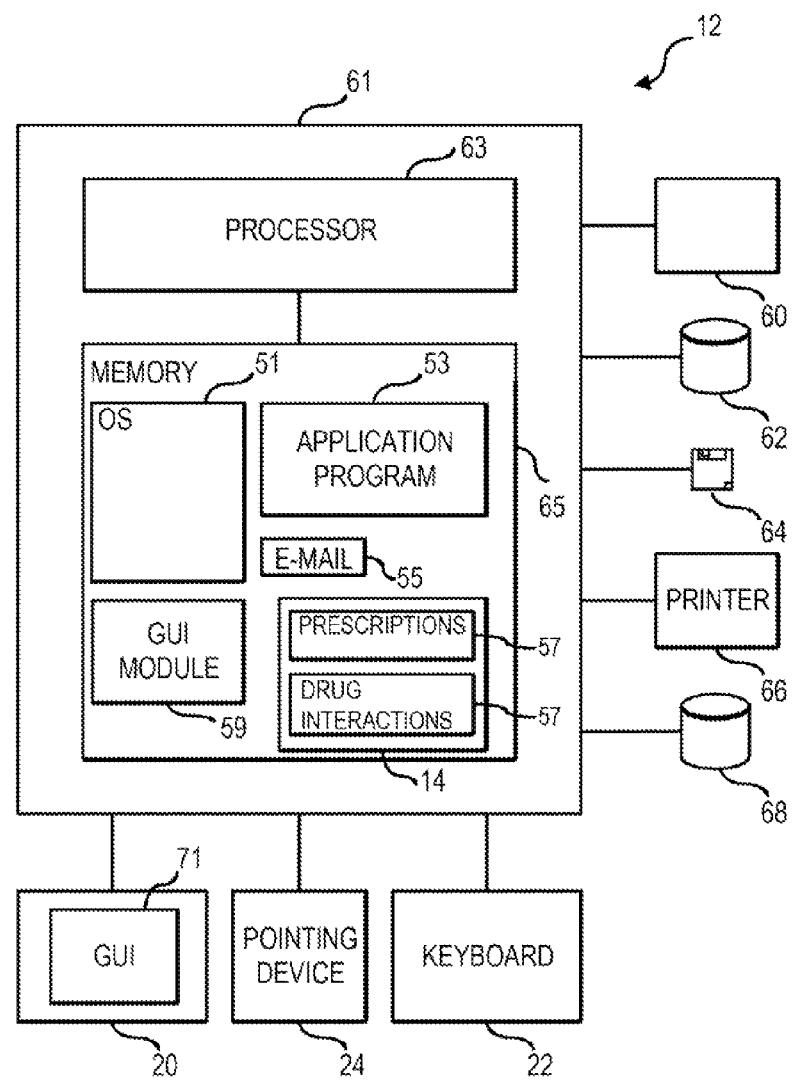
FIG. 2 illustrates an exemplary local server depicted as part of the system shown in FIG. 1.

FIG. 2 hereafter provides an exemplary local server 12 in which the mechanisms of the following embodiments may be implemented. It should be appreciated, however, that FIG. 2 is only exemplary and is not intended to state or imply any limitation as to the particular architectures in which the exemplary aspects of the various embodiments may be implemented. Many modifications to the architecture depicted in FIG. 2 may be made without departing from the scope and spirit of the following description and claimed subject matter.

FIG. 2 illustrates an exemplary local server 12 that can be used to implement embodiments of the present invention. Local server comprises a computer 61. The computer 61 includes a processor 63 and a memory 65, such as random access memory (RAM). The computer 61 is operatively coupled to a display 20 (such as through workstation 26, FIG. 1), which presents images such as windows to the user on the GUI 71. The computer 12 may be coupled to other devices, such as keyboard 22, mouse device 24, a printer 66, etc. Of course, those skilled in the art will recognize that any combination of the above components, or any number of different components, peripherals, and other devices, may be used with the computer 61.

Generally, the computer 61 operates under control of an operating system (OS) 51 (e.g. z/OS, OS/2, LINUX, UNIX, WINDOWS, MAC OS) stored in the memory 65, and interfaces with the user to accept inputs and commands and to present results, for example through a GUI module 59. Although the GUI module 59 is depicted as a separate module, the instructions performing the GUI functions can be resident or distributed in the operating system 51, an associated application program 53, or implemented with special purpose memory and processors. The computer 61 also implements an email application/server 55 for providing email notification from the medical professional to the patient, or vice-versa.

Database 14 is operational on computer 61, and resides in memory 65 in the depicted embodiment. The database 14 as shown includes prescription and drug interaction data 57 associable with a particular patient. Database 14 may also store data collected during online patient consultation. Database 14 may also store offline results monitored on behalf of the patient through data analysis using the application program 53. The computer 61 also optionally comprises an external data communication device 60 such as a modem, satellite link, Ethernet card, wireless link or other device for communicating with other computers, e.g. via the Internet or other network.

Data storage device 62 is a direct access storage device (DASD) 62, including one or more primary volumes holding a number of datasets. DASD 62 may include a number of storage media, such as hard disk drives (HDDs), tapes, and the like. Data storage device 62 may also include a number of storage media in similar fashion to device 62. The device 68 may be designated as a backup device 68 for holding backup versions of the number of datasets primarily stored on the device 62. As the skilled artisan will appreciate, devices 62 and 68 need not be located on the same machine. Devices 62 may be located in geographically different regions, and connected by a network link such as Ethernet (such as incorporated into subsystem 28 (FIG. 1)). Devices 62 and 68 may include one or more volumes, with a corresponding volume table of contents (VTOC) for each volume.

In one embodiment, instructions implementing the operating system 51, the computer program 53, and the database 14 are tangibly embodied in a computer-readable medium, e.g., data storage device 62, which may include one or more fixed or removable data storage devices, such as a zip drive, disk 64, hard drive, DVD/CD-ROM, digital tape, etc., which are generically represented as the disk 64. Further, the operating system 51 and the computer program 53 comprise instructions which, when read and executed by the computer 61, cause the computer 61 to perform the steps necessary to implement and/or use the present invention. Computer program 53 and/or operating system 51 instructions may also be tangibly embodied in the memory 65 and/or transmitted through or accessed by the data communication device 60. As such, the terms "article of manufacture," "program storage device" and "computer program product" as may be used herein are intended to encompass a computer program accessible and/or operable from any computer readable device or media.

Embodiments of the present invention may include one or more associated software application programs 53 that include, for example, functions for managing a distributed computer system comprising a network of computing devices, such as a storage area network (SAN) as part of data storage subsystem 28 (FIG. 1). The program 53 may operate within a single computer 61 or as part of a distributed computer system comprising a network of computing devices (such as computer 61 and workstation 26, FIG. 1). The network may encompass one or more computers connected via a local area network and/or Internet connection (which may be public or secure, e.g. through a VPN connection), or via a fibre channel Storage Area Network or other known network types as will be understood by those skilled in the art. (Note that a fibre channel SAN is typically used only for computers to communicate with storage systems, and not with each other.)

The local server 12 may process instructions from the medical professional to the patient, or operational commands for the diagnostic tool 54 (FIG. 1) into commands that are sent over the network from the local server 12 to the patient. A portion of the commands may relate to directions that are provided to the patient, such as directions for installation of the diagnostic tool in the network device. The local server, the network device, the patient interface, or an additional device may process these commands. An additional portion of the commands may relate to operation of the diagnostic tool itself. For example, a physician may remotely operate the diagnostic tool by use of the interface 18 and with the assistance of the patient.

Figure 3:
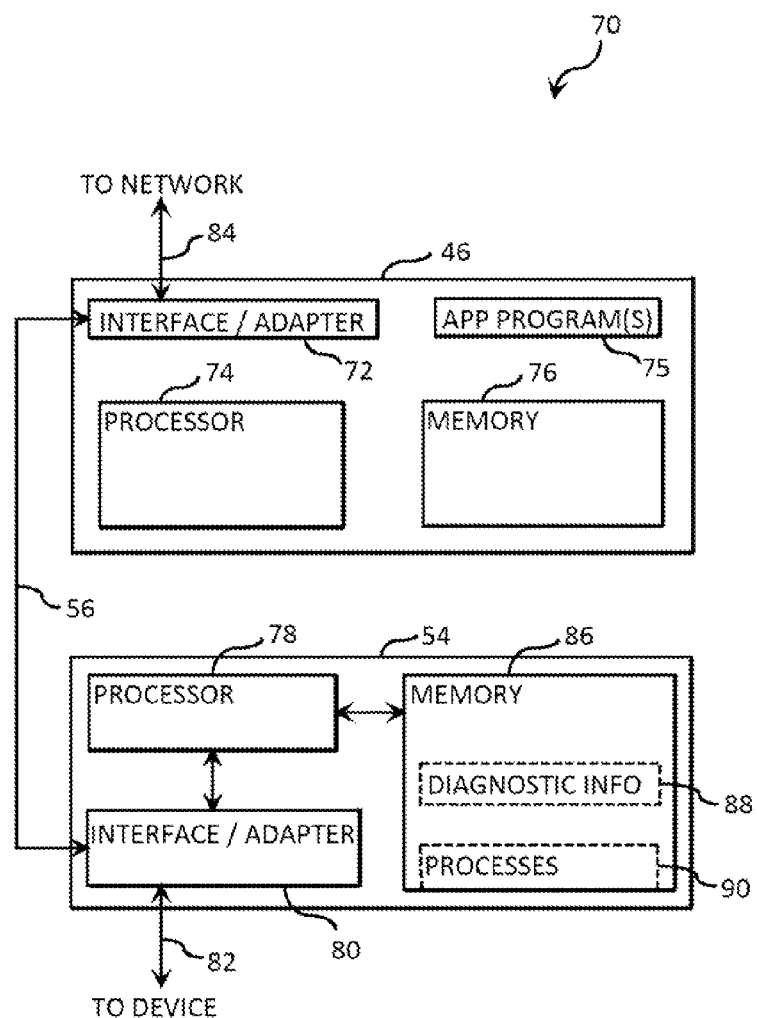
FIG. 3 illustrates an exemplary network device connected to an exemplary modular diagnostic tool.

Turning to FIG. 3, an exemplary network patient-side portion 70 of system 10 (FIG. 1) is depicted, showing an exemplary network device 46 in communication with a diagnostic tool 54. Network device 46 includes one or more application programs 75 implemented to facilitate communication between the network device 46 and another component over the network link 84, such as the patient interface 34 (FIG. 1) using interface/adapter 72. Network device 46 includes a processor 74 and onboard memory 76, operational in many respects similar to that of local processor 12. Interface/adapter 72 (such as a network adapter 72) provides communication over a standardized communication link 56, such as a USB connection with the diagnostic tool 54. Adapter 72 is also coupled to the patient interface 34, network 30, or both (FIG. 1) over network link 84.

As the skilled artisan will appreciate, the standardized communication link may include a variety of communications mechanisms. For example, the standardized communications link may be compliant with a universal serial bus (USB) communications protocol, an internet protocol (IP), an Institute for Electrical and Electronics Engineers (IEEE) wired or wireless communications protocol, a wireless application protocol (WAP), a local area network (LAN) protocol, a wide area network (WAN) protocol, a global system for mobile communication (GSM) protocol, and an AppleTalk® protocol.

In one embodiment, processor 74 receives the broadcast commands from the local server 12, interpreting them as commands for control of the diagnostic tool, or instructions to be disseminated to the patient. Control commands are forwarded over the link 56 to the diagnostic tool 54. Instructions may be provided to the patient interface over link 84, where they may be converted to text, audio and video that is displayed to the patient over GUI 36 (FIG. 1). In some embodiments, network device 46, in cooperation with the patient interface 34, local server 12, medical professional interface 18, etc., may implement a voice-over-internet-protocol (VOIP) exchange, webcam session, voice or text chat session, and the like between the patient and medical professional. In this way, the patient may engage in dialogue or text communication with the medical professional during a particular session.

Returning to FIG. 3, tool 54 also includes a processor 78 coupled to a memory device 86, as well as an integrated interface/adapter 80. Memory 86 is capable of storing diagnostic information 88, as well as application processes 90 that are executed in certain scenarios as will be explained, following. Interface/adapter 80 again functions as a communications interface between one or more interconnected biometric devices (such as a heart rate monitor) and the tool 54 over communications link 82. Interface/adapter 80 also provides for communication between the tool 54 and the network adapter 46.

In one embodiment, the processor 78, in certain scenarios, executes one or more processes 90. For example, the tool 54 may execute one of the processes 90 to upload diagnostic information 88 stored in the memory 86 through the network adapter 46 to the medical professional once a determination is made that the tool 54 is connected over link 56 with the network device 46, and through link 84 with the local server 12.

Figure 4:
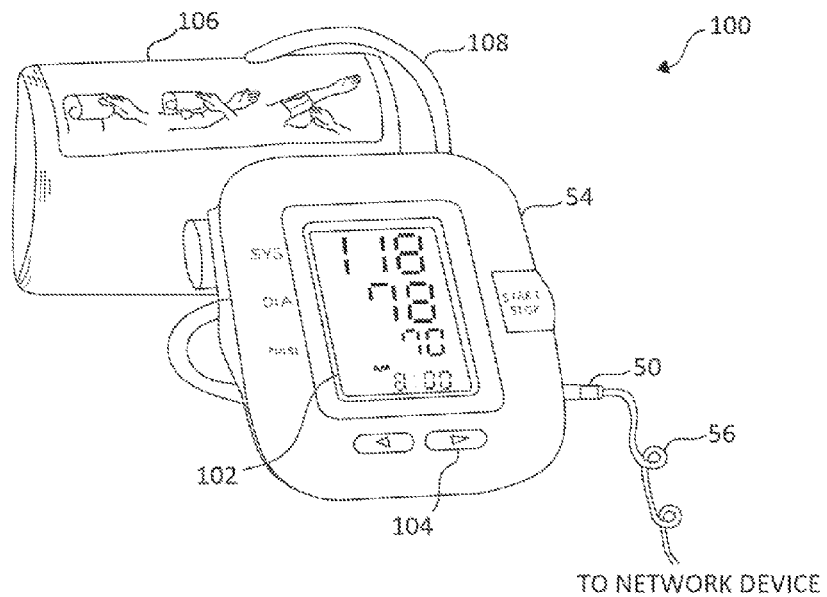
FIG. 4 illustrates an exemplary modular diagnostic tool for obtaining blood pressure biometric information.

Turning now to FIG. 4, an exemplary blood pressure monitor 100 is shown as one of an available number of modular diagnostic tools 54. Blood pressure monitor 100 includes an LCD display 102 for displaying systolic information, diastolic information, and time. Monitor 100 also includes user input buttons 104, cuff 106, and hose 108 for providing air pressure to expand cuff 106. As the skilled artisan will appreciate, the illustrated tool 54 includes the electronic subcomponents necessary to perform blood pressure testing on a patient. Monitor 100 is made modular by USB communications link 56 implementing USB connector 50 between tool 54 and network device 46 (FIG. 3).

Figure 5:
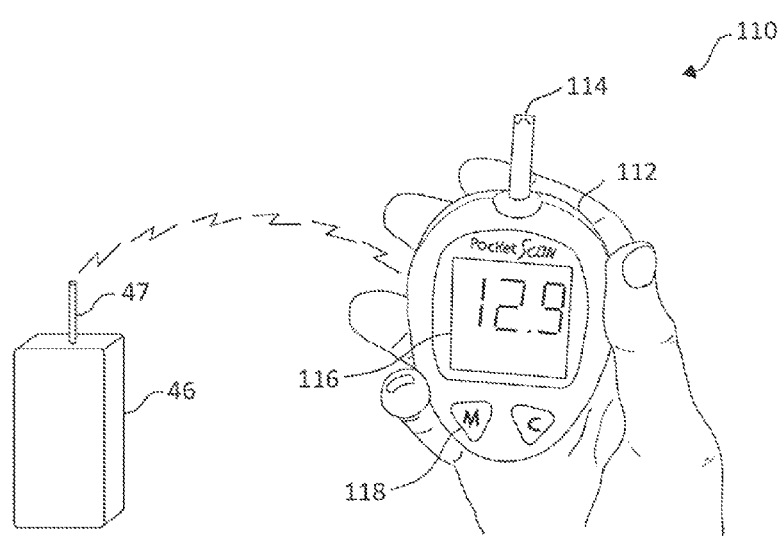
FIG. 5 illustrates an additional exemplary modular diagnostic tool for obtaining blood glucose biometric information.

Turning to FIG. 5, an exemplary blood glucose meter 110 is depicted as an additional example of a modular diagnostic tool communicable with the network device. In the depicted embodiment, the glucose meter 110 establishes a wireless communications link with an antenna 47 of the network device 46 using a standardized communications link such as 802.11a/b/g or an equivalent. Meter 110 includes a housing 112, a probe 114 for taking blood readings, display 116, and input buttons 118. Example operations of the monitor 100 and meter 110 will be further described, following.

Figure 6:
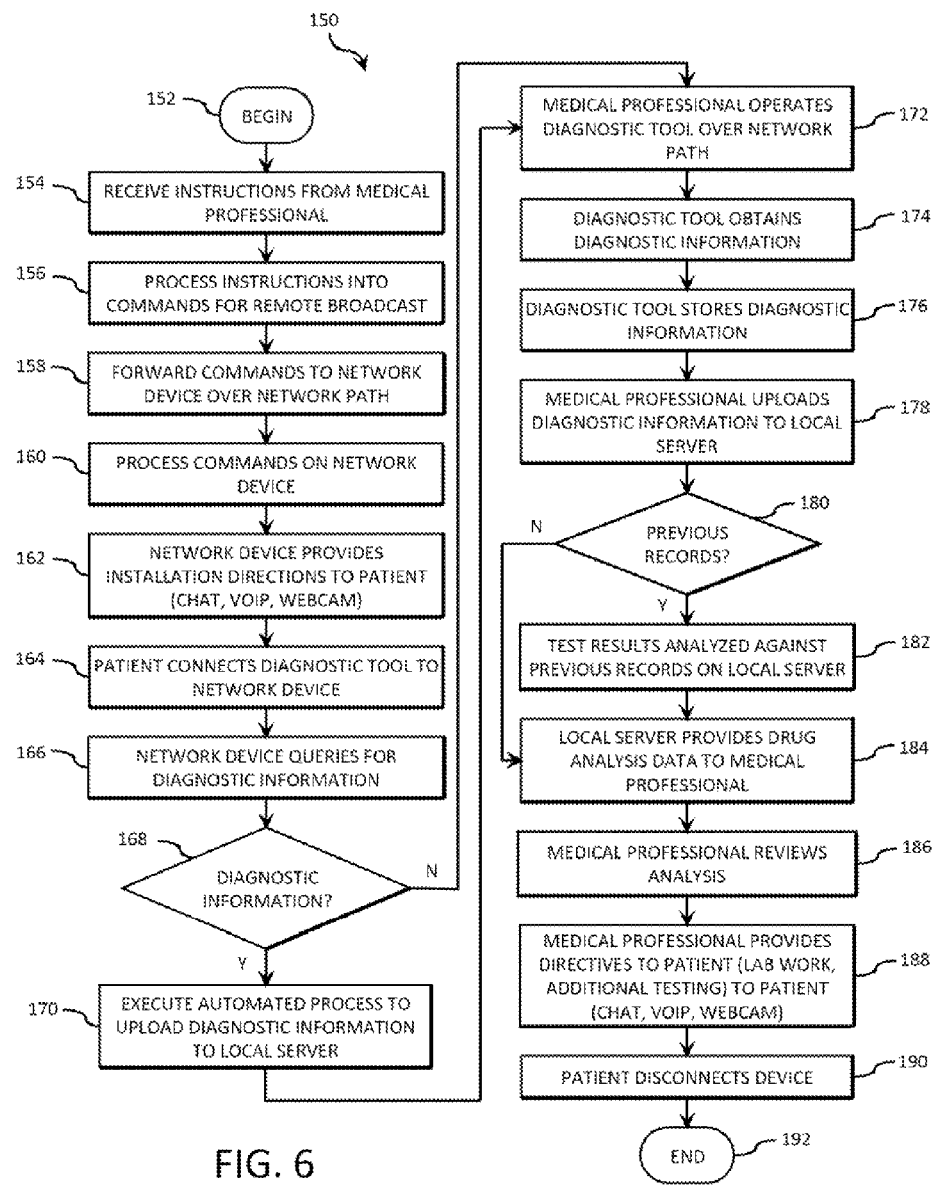
FIG. 6 illustrates an exemplary method for online monitoring of a remote patient.
Figure 7:
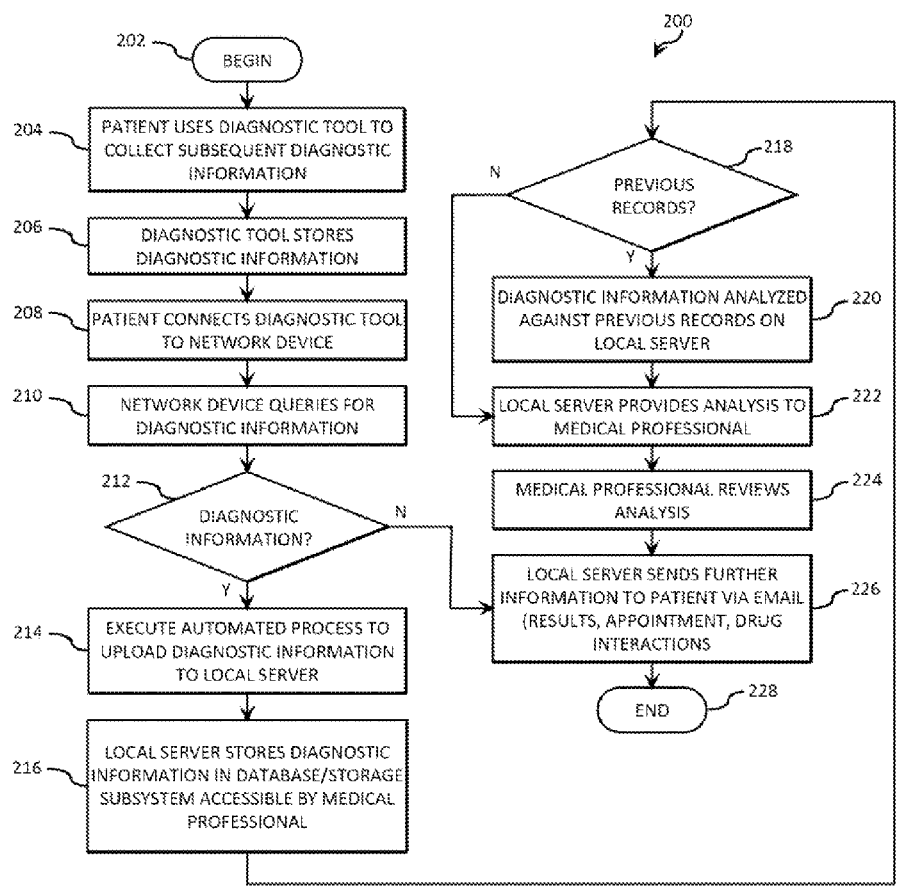
FIG. 7 illustrates an exemplary method of offline collection for subsequent uploading diagnostic information of a patient.

Turning to FIGS. 6 and 7, various methods are depicted as examples of online patient monitoring/offline data collection using the mechanisms of the present invention. As one skilled in the art will appreciate, various steps in these methods may be implemented in differing ways to suit a particular application. In addition, the described methods may be implemented by various means, such as hardware, software, firmware, or a combination thereof operational on or otherwise associated with the storage environment. For example, the methods may be implemented, partially or wholly, as a computer program product including a computer-readable storage medium having computer-readable program code portions stored therein. The computer-readable storage medium may include disk drives, flash memory, digital versatile disks (DVDs), compact disks (CDs), and other types of storage mediums.

Turning first to FIG. 6, method 150 begins (step 152) by the interface associated with the medical professional receiving input/instructions from the medical professional (step 154). The input may take place as the medical professional operates an input device connected to the workstation previously described. As a following step, the instructions are processed by the local server into commands for remote broadcast (step 156).

The commands are forwarded by the local server to the network device over a network path (step 158) where they are processed by the network device (step 160). As a part of processing the commands, the network device provides installation direction to the patient for connecting the modular diagnostic tool into the network device (step 162). This direction may be pursuant to one of several communications schemes, such as a text or voice chat, VOIP communication, or a webcam session.

Pursuant to the installation directions, the patient connects the diagnostic tool that was supplied to them by the medical professional (step 164). The network device initializes the diagnostic tool for operation. The network device recognizes the diagnostic tool (for example, over a Bluetooth® communications channel or by recognition of a USB port insertion), and executes an automated process to query the tool for any diagnostic information stored on the device (step 166). If the network device determines that diagnostic information is available (step 168), the diagnostic tool, either by itself or in conjunction with the network device, executes an automated process to upload the diagnostic information through the network device to the local server (step 170).

As a following step, the medical professional proceeds to operate the diagnostic tool over the network path using the network device (step 172). For example, the patient may, at the request of the medical professional, install the cuff of a blood pressure monitor. The medical professional may then perform some initialization functions remotely over the network path, and then operate the monitor by causing the cuff to expand with air and take readings as the cuff is slowly relieved of air pressure. In this fashion, the medical professional has the ability to perform medical services on a live basis with the assistance of the patient.

Once the readings are taken, the diagnostic tool stores the information in onboard memory (step 176). The medical professional then uploads the diagnostic information, through the network device, to the local server (step 178). If the local server determines that previous medical records/information is available for this particular patient (step 180), then the diagnostic information, such as test results, are analyzed against the previous information (step 182). In any event, the local server, in cooperation with database 14 (FIGS. 1, 2) analyzes the data and provides to the medical professional. In one embodiment as shown, the analysis data provided to the medical professional may include a drug analysis obtained by comparing patient drug information (e.g., prescriptions assigned to the patient) with stored drug interaction data (step 184). In other embodiments, the analysis data may include recommendations for the medical professional to suggest laboratory work or additional testing to the patient.

The medical professional reviews the analysis data and/or recommendations provided by the local server (step 186). Based on the analysis data, the medical professional provides directives to the patient (step 188), such as suggestions to obtain additional lab work, additional testing, schedule an on-site visit, and the like. Again, these directives may be provided pursuant to the communications scheme engaged in previously, such as VOIP, voice/text chat, and webcam session. The patient then disconnects the diagnostic tool (step 190), and the method 150 then ends (step 192).

Turning now to FIG. 7, method 200 illustrates exemplary offline data collection capabilities of the modular diagnostic tool. Method 200 begins (step 202), with the patient using the tool to collect diagnostic information subsequent to the online exchange with the medical professional described previously in method 150 (FIG. 6) (step 204). For example, the patient may continue to take blood pressure and/or blood glucose readings.

As a next step, the diagnostic tool stores the diagnostic information in onboard memory as previously described (step 206). At a later time, the patient connects the diagnostic tool (e.g., wired or wireless) to the network device (step 208). Here again, the network device recognizes the diagnostic tool on its network and queries the diagnostic tool for information (step 210). If diagnostic information is determined to be stored on the device (step 212), an automated process is executed to upload the diagnostic information through the network device to the local server (step 214) where it is accessible by the medical professional.

The local server stores the diagnostic information in its database (either locally or on an associated data storage subsystem) accessible by the medical professional (step 216). If previous medical records/information is available in the system for the patient (step 218), the diagnostic information obtained from the instant situation is analyzed against the previous information (step 220). Here as before, this analysis is provided to the medical professional for review in the form of recommendations, drug analysis information, etc. (step 222). The medical professional reviews the analysis (step 224).

The diagnostic tool may provide information to the medical professional in a variety of scenarios. For example, at a particular time, diagnostic information may not be obtained from the patient (again, step 212), but time may have elapsed for the patient to obtain such diagnostic information (such as an additional blood glucose test). Based on operation of application program(s) executed on the local server per a particular situation (such as appointment scheduling, test scheduling, data analysis, drug analysis, calendaring, input from the medical professional, and the like), the local server sends further information to the patient via the local server's associated email server (step 226). This further information may include such information as test results, appointment information, drug analysis, notices, invoices, etc. For example, based on particular blood glucose results obtained by the patient over a period of time, the local server may determine that an immediate follow-up appointment is warranted. The local server may check the calendar of the medical professional and query the patient for an appointment date. Once the patient verifies the appointment date, the date is scheduled in the system's calendar and a notification is emailed to the patient and/or medical professional. In addition, the system and/or the medical professional may interpret the glucose results. The results may then be similarly forwarded to the patient.

While the foregoing methods 150 and 200 provide exemplary functionality of the mechanisms of the present invention, the skilled artisan will appreciate that similar functionality may be carried out using the flexibility provided by the modular diagnostic tool. For example, the patient may visit a laboratory and obtain testing that may be stored on the diagnostic tool's onboard memory. Once the patient returns home, they may reconnect the diagnostic tool to the local server. Once the diagnostic tool is again recognized by the network device, the automated processes may again be executed to upload the laboratory data to the local server for collection and analysis by the medical professional. In additional embodiments, the patient interface 34, network device 46, and/or diagnostic tool 54 (FIGS. 1, 3) may be adapted to contact emergency medical personnel in case of a medical emergency, such as a paramedic team or hospital emergency room. For example, if a patient provides diagnostic information indicating a medical emergency, appropriate responding personnel may be contacted. The diagnostic information may be electronically forwarded to the responding personnel for analysis.

Some of the functional units described in this specification have been labeled as modules in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, as electronic signals on a system or network.

While one or more embodiments of the present invention have been illustrated in detail, the skilled artisan will appreciate that modifications and adaptations to those embodiments may be made without departing from the scope of the present invention as set forth in the following claims.

What is claimed is:

1. A computer implemented system for performing remote monitoring of a patient during a routine checkup, comprising:
 a local server configured for receiving instructions from a medical professional and processing the instructions into commands for remote broadcast;
 a network device in remote communication with the local server, the network device configured for processing the commands for remote broadcast received from the local server; and
 at least one modular diagnostic tool communicable with the network device over a standardized communications link, the at least one modular diagnostic tool configured for obtaining diagnostic information from the patient, wherein:
  a first portion of the commands for remote broadcast includes directions to the patient for installation of the at least one modular diagnostic tool in the network device,
  the at least one modular diagnostic tool is initialized for operation by the network device,
  the at least one modular diagnostic tool is operable by the medical professional based on a second portion of the commands for remote broadcast to obtain the diagnostic information, and
  the network device, when connected with the at least one modular diagnostic tool over the standardized communications link, executes an automated process to upload the diagnostic information to the local server for collection and analysis by the medical professional.

2. The computer implemented system of claim 1, wherein the at least one modular diagnostic tool is one of an available plurality of modular diagnostic tools configured for being provided to the patient by the medical professional, each of the available plurality of modular diagnostic tools communicable with the network device over the standardized communications link.

3. The computer implemented system of claim 1, wherein the network device is further configured to be communicable with a computing device of the patient as a client, the network device utilizing a communications channel associated with computing device to forward the diagnostic data from the at least one modular diagnostic tool to the local server.

4. The computer implemented system of claim 1, wherein the standardized communications link is compliant with at least one of a universal serial bus (USB) communications protocol, an internet protocol (IP), an Institute for Electrical and Electronics Engineers (IEEE) wired or wireless communications protocol, a wireless application protocol (WAP), a local area network (LAN) protocol, a wide area network (WAN) protocol, and a global system for mobile communication (GSM) protocol.

5. The computer implemented system of claim 1, further including a data storage subsystem in communication with the local server for storing at least a portion of the diagnostic information.

6. The computer implemented system of claim 3, wherein the local server is configured to perform at least one of:
 comparing patient prescription information with drug interaction data to generate a drug analysis accessible by at least one of the medical professional and the patient, and
 comparing the diagnostic information against additional diagnostic information previously stored by the local server to generate an analysis provided to the medical professional.

7. The computer implemented system of claim 1, further including at least one of: (1) an email server configured to be operable on the local server for providing at least one of the diagnostic information, scheduling information, notifications, reminders, and alerts to at least one of the patient and the medical professional, and (2) a local memory configured to be operable on the at least one modular diagnostic tool for storing additional diagnostic information obtained from operation of the at least one modular diagnostic tool remote from the standardized communications link.

8. The computer implemented system of claim 1, wherein the at least one modular diagnostic tool includes at least one of a blood pressure monitor, pulse oximeter, blood glucose meter, scale, thermometer, otoscope, ophthalmoscope, body fat monitor, heart rate monitor, stethoscope, alcohol screening device, fingerprint scanner, retinal scanner, and pH meter.

9. A computer implemented method for performing remote monitoring of a patient during a routine checkup by at least one processor device in communication with a memory device, comprising:

receiving instructions from a medical professional on a local server;

processing the instructions into commands for remote broadcast;

forwarding the commands for remote broadcast to a network device over a network path;

processing the commands for remote broadcast received from the local server on the network device;

directing the patient to install a modular diagnostic tool in the network device using a first portion of the commands for remote broadcast;

initializing the modular diagnostic tool for operation and communication with the network device over a standardized communications link;

operating the modular diagnostic tool by the medical professional over the network path using a second portion of the commands for remote broadcast to obtain diagnostic information; and upon a communications connection between the modular diagnostic tool and the network device, executing an automated process to upload the diagnostic information from the modular diagnostic tool to the local server for collection and analysis by the medical professional.

10. The computer implemented method of claim 9, further including associating the network device with a computing device of the patient as a client, wherein forwarding the diagnostic information by the network device over the network path to the local server includes using a communications channel associated with the computing device of the patient as at least a portion of the network path.

11. The computer implemented method of claim 9, further including storing the diagnostic information in a local memory on the modular diagnostic tool.

12. The computer implemented method of claim 9, further including storing at least a portion of the diagnostic information on a storage device in a data storage subsystem associated with the local server.

13. The computer implemented method of claim 9, further including at least one of:

comparing patient prescription information with drug interaction data to generate a drug analysis accessible by at least one of the medical professional and the patient, and comparing the diagnostic information against additional diagnostic information previously stored by the local server to generate an analysis provided to the medical professional.

14. The computer implemented method of claim 9, further including at least one of:

providing at least one of the diagnostic information, scheduling information, notifications, reminders, and alerts to at least one of the patient and the medical professional via email, and enabling interaction between the medical professional and the patient over the network path using at least one of a chat application, a voice over internet protocol (VOIP) application, and a web cam application.

15. A computer program product for performing remote monitoring of a patient during a routine checkup by at least one processor device in communication with a memory device, the computer program product comprising a non-transitory computer-readable storage medium having computer-readable program code portions stored therein and executed by a processor device, the computer-readable program code portions comprising:

a first executable portion for receiving instructions from a medical professional on a local server;

a second executable portion for processing the instructions into commands for remote broadcast;

a third executable portion for forwarding the commands for remote broadcast to a network device over a network path;

a fourth executable portion for processing the commands for remote broadcast received from the local server on the network device;

a fifth executable portion for directing the patient to install a modular diagnostic tool in the network device using a first portion of the commands for remote broadcast;

a sixth executable portion for initializing the modular diagnostic tool for operation and communication with the network device over a standardized communications link;

a seventh executable portion for operating the modular diagnostic tool by the medical professional over the network path using a second portion of the commands for remote broadcast to obtain diagnostic information; and an eighth executable portion for, upon a communications connection between the modular diagnostic tool and the network device, performing an automated process on the network device to upload the diagnostic information from the modular diagnostic the local server for collection and analysis by the medical professional.

16. The computer program product of claim 15, further including a ninth executable portion for associating the network device with a computing device of the patient as a client, wherein forwarding the diagnostic information by the network device over the network path to the local server includes using a communications channel associated with the computing device of the patient as at least a portion of the network path.

17. The computer program product of claim 15, further including a ninth executable portion for storing the diagnostic information on a medical database configured to be operable on the local server.

18. The computer program product of claim 17, further including a tenth executable portion for storing at least a portion of the medical database on a storage device in a data storage subsystem.

19. The computer program product of claim 15, further including a ninth executable portion for performing at least one of:

comparing patient prescription information with drug interaction data to generate a drug analysis accessible by at least one of the medical professional and the patient, and comparing the diagnostic information against additional diagnostic information previously stored by the local server to generate an analysis provided to the medical professional.

20. The computer program product of claim 15, further including a ninth executable portion for providing at least one of the diagnostic information, scheduling information, notifications, reminders, and alerts to at least one of the patient and the medical professional via email.

\* \* \* \* \*